United States Patent [19]
Crawford, Jr.

[11] Patent Number: 5,331,549
[45] Date of Patent: Jul. 19, 1994

[54] MEDICAL MONITOR SYSTEM

[76] Inventor: John M. Crawford, Jr., 15 Water St., Clinton, Hunterdon County, N.J. 08809

[21] Appl. No.: 922,577

[22] Filed: Jul. 30, 1992

[51] Int. Cl.$^5$ .............................................. G06F 15/42
[52] U.S. Cl. .......................... 364/413.02; 364/413.01; 364/413.03
[58] Field of Search ...................... 364/413.03, 413.02, 364/413.01

[56] References Cited

U.S. PATENT DOCUMENTS

| | | | |
|---|---|---|---|
| 4,051,522 | 9/1977 | Healy et al. | 358/86 |
| 5,121,470 | 6/1992 | Trautman | 395/140 |
| 5,199,439 | 4/1993 | Zimmerman et al. | 128/670 |

Primary Examiner—Roy N. Envall, Jr.
Assistant Examiner—Ari M. Bai
Attorney, Agent, or Firm—McAulay Fisher Nissen Goldberg & Kiel

[57] ABSTRACT

A medical monitoring system in which a plurality of vital signs monitors for a plurality of patients provide data on a continuing basis to a central server which in turn provides supervisory screen display that indicates the normal status or varying levels of alarm status of individual patients. The system permits an overview display of a floor and also provides a zoom-in display of an individual site patient together with an indication of a limited number of vital signs and a warning alarm signal when any one or more vital signs is outside of a first warning set of predetermined limits or a more critical alarm set of predetermined limits.

18 Claims, 7 Drawing Sheets

POP-UP WINDOW VIEW

PATIENT STATUS
- ● Level 1 - sporadic monitoring (ambulatory, non-critical)
- ○ Level 2 - semi-continous (semi-ambulatory, non-critical)
- ○ Level 3 - continous monitoring (non-ambulatory, critical)

[OK]  [Cancel]    —70

RESET ALL BED PARAMETERS

This button will reset all bed parameters to their default values. This includes signs selected, sign limits, patient age and status, and dial-out options.

Are sure you want to do this?

[OK]  [Cancel]

TELECOMMUNICATIONS DIAL-OUT OPTIONS
- ☐ Deliver signs to central station   1 908 735 2727
- ☒ Deliver alarms to central station   1 908 735 2727
- ☒ Deliver alarms to pager   1 800 222 4286 3594

[OK]  [Cancel]

SET VITAL SIGN LIMITS      65

| SIGN | Warning low | Warning high | Critical low | Critical high |
|---|---|---|---|---|
| Diastolic pressure | 90 | 220 | 50 | 270 |
| Systolic pressure | 50 | 180 | 30 | 230 |
| Pulse rate | 35 | 130 | 250 | 180 |
| Respiration rate | 4 | 70 | 2 | 130 |
| Body temperature | 92 | 102 | 85 | 105 |
| Oxygen saturation | 60 | n/a | 20 | n/a |

68—○ Child    ● Adult    ○ Senior
        67   66        69

[OK]  [Reset]  [Cancel]

SELECT VITAL SIGNS
- ☒ Blood pressure
- ☒ Pulse Rate
- ☒ Respiration Rate
- ☒ Body Temperature
- ☒ Oxygen Saturation
- ☒ All Signs

[OK]  [Cancel]

MEDICAL MONITOR SYSTEM

BACKGROUND OF THE INVENTION

This invention relates to, in general, a supervisory system that monitors the vital signs of patients at home or in a health-care facility.

There is currently no cost effective means of continuously supervising an entire building full of patients from a central point. Accordingly, several problems have developed with patient care. When an emergency situation develops, it must be detected by supervisory staff before it can be dealt with. After detection, the response to emergencies can only occur after the proper professionals have been informed, and the problem is diagnosed. This process can take from several minutes to several hours, even in a fully-staffed hospital. There is no feasible way to employ the number of staff required to effectively supervise patients located in hundreds of separate rooms throughout a facility.

The inability to record the vital signs of patients (located outside Intensive Care Units) on a 24-hour basis leads to problems with medical analysis. Individual readings can be missed or conducted improperly, leading to inaccurate interpretation of results. Lengthy time intervals between readings increase the probability that smaller trends will be missed, and that errant readings will alter results. Difficulties in manually storing and retrieving the results of hundreds or thousands of tests make it nearly impossible to examine several consecutive weeks or months of a patient's vital signs.

When a substantial distance, such as several miles, separates a doctor from his or her patients, all these problems increase by several magnitudes. Outpatients are rarely examined more than a few times a week, so their medical emergencies often go entirely undetected. When outpatient problems are discovered, it takes several times longer for the proper personnel to diagnose and respond to the condition than it would for inpatients. Medical trend analysis is also much less effective and accurate for outpatients.

Existing electronic means of patient monitoring have been developed to avoid such difficulties, such systems typically consist of high-cost intelligent patient monitors linked together in local area networks. However, because of design and capability limitations, these systems do not serve as feasible, cost-effective, facility-wide central monitoring systems. They are typically more suited for limited numbers of patients requiring specific services.

Current solutions generally suffer from several shortcomings. The high cost of these systems prohibits the purchase of sufficient resources to monitor entire health-care facilities, or renders such purchases as non cost-effective. They do not have the power to effectively supervise large numbers of patients simultaneously, especially over expansive geographic areas. They do not provide the flexibility needed to account for various levels of patient mobility, to easily and quickly re-distribute resources such as patient monitors to new locations, or to efficiently upgrade system capacity as technology improves. Existing systems are difficult for non-technical personnel to learn and operate, and they do not provide the fault-tolerance for operator error/abuse and equipment failure which is needed in a critical medical application. Furthermore, the selection and presentation of the data gathered by these systems does not facilitate the effective supervision of large numbers of patients.

A major purpose of this invention is to provide a system which provides an optimum selection of data to be presented and optimum arrangement of that data so as to make feasible and useful the monitoring of a large number of patients in a fashion that increases the likelihood and enhances the ability of having an immediate response to conditions which require immediate response.

Another purpose of this invention is to employ known, low-cost, standard types of units, in a configuration which provides the capacity to monitor large numbers of patients, allows for the flexible, dynamic distribution of resources, provides sufficient fault-tolerance, and permits the efficient upgrade of system components as component design increases capacity of data handling, sensitivity, and scope of vital signs monitored.

More specifically, it is a purpose of this invention to 1) provide earlier detection and diagnosis of medical emergencies, 2) provide better warning and notification of patient emergencies, 3) reduce the time interval between readings of vital signs, 4) reduce the number of staff required to supervise patients, 5) provide better historic records of vital signs, 6) allow greater accuracy in medical trend analysis when compared to present methods, and 7) to provide the above at a cost which makes it feasible for an institution to adopt the system.

BRIEF DESCRIPTION

This invention gathers data on patient vital signs using portable bedside medical monitors. As the data is collected, it is sent to a central computer.

Using the computer, users can examine the current or past vital signs of any patient simply by selecting the patient's room from a geographic facility map displayed on a computer screen (CRT). The system will also alert users when the monitored signs of any supervised patient go above or below preset limits. Should such conditions occur, the system will flash a warning display on its CRT describing the emergency. The system also illustrates the location of the emergency by highlighting the proper room on the facility map.

With the emergency located on a overview floor screen, the attendant can select an individual bed or site screen which provides more detailed information on the patient having the emergency.

Other options for notification of patient emergencies include paging doctors and nurses with alphanumeric pagers, and dialing out over telephone lines to alert external parties. This feature enables doctors or other healthcare professionals in a central building to supervise patients in remote facilities, or even their own homes. This invention can also transmit live video of outpatients over telephone lines, for doctor viewing.

Workstations allow users located away from the main computer to have access to all system functions. Patient data is stored at regular intervals, allowing future retrieval of readings, and detailed medical trend analysis.

This system allows one person to monitor the vital signs of hundreds of patients located in separate rooms on various floors of a facility, substantially reducing the number of staff required for such a purpose. Because the location and exact condition of monitored emergencies are known the instant problems are detected, effective response time to medical emergencies is substantially reduced. The system's abilities to display and graph all past readings (taken 24 hours a day) makes the analysis of vital signs and medical trends much more effective and accurate. These benefits are several magnitudes greater for patients located in other buildings or other towns, since distance and lack of supervisory staff compound problems with analysis of medical trends, detection of emergencies, and response time to those emergencies.

BRIEF DESCRIPTION OF THE FIGURES

FIG. 6 illustrates various windows which can be called up by the user to facilitate user selection of options and modification of operating parameters.

DESCRIPTION OF THE PREFERRED EMBODIMENTS

Figure 1:
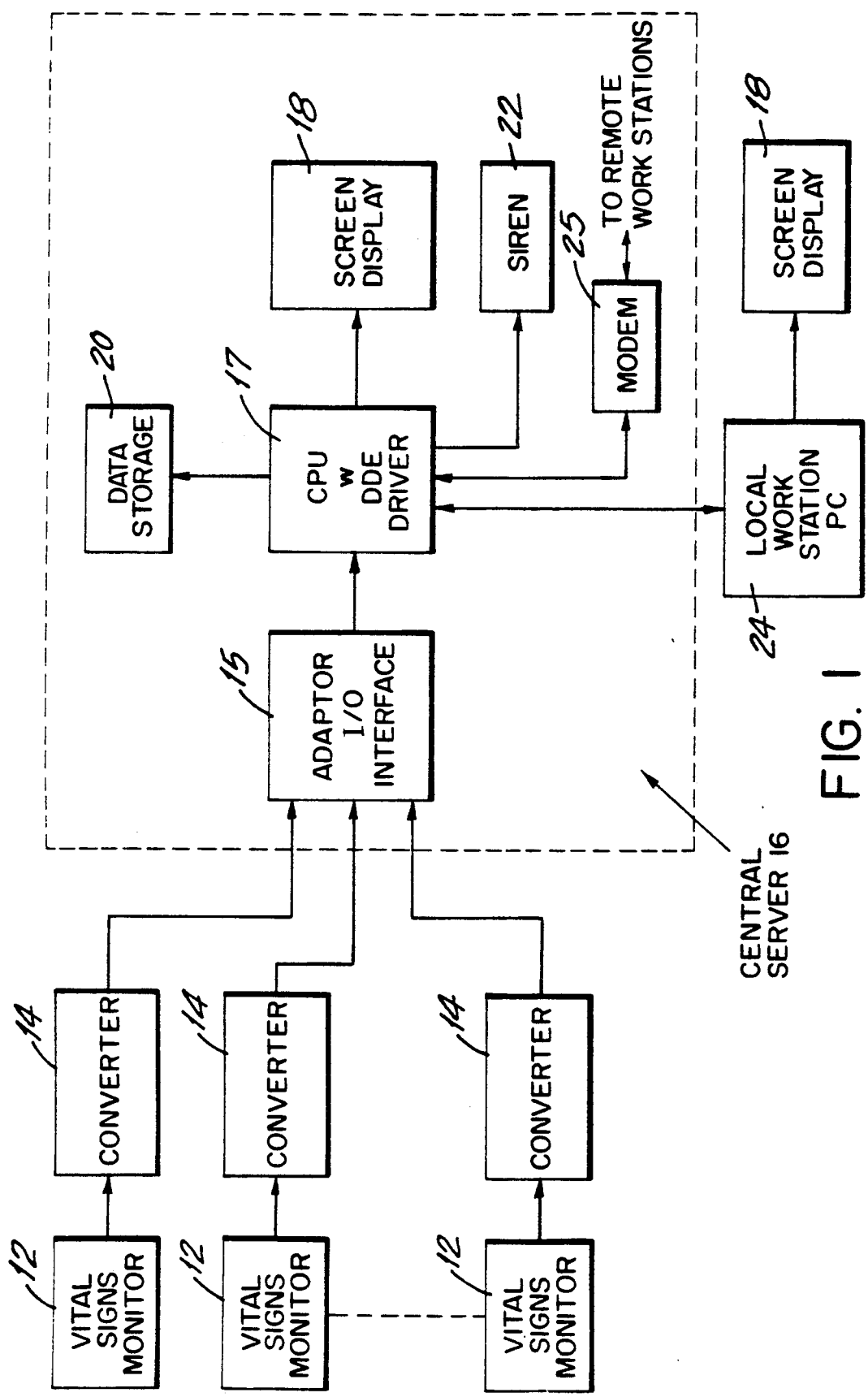
FIG. 1 is a block diagram of the overall system arrangement of this invention.

As shown in FIG. 1, a plurality of vital sign monitors 12 are coupled through converters 14 to a central server 16. The central server 16 essentially consists of a fault tolerant PC compatible central processing unit 17 (CPU) with appropriate programming including a DDE driver, monitoring application software and preferably a remote control communication software. At the central server 16, a screen display 18 is provided and is a critical part of the system of this invention. The screen display is what provides the appropriate selected information to facilitate response to various out of normal range conditions. The screen displays are described in greater detail in connection with FIGS. 3 through 8 herein. A data storage 20 is employed to store data so that it can be retrieved and reviewed for analysis that is deemed appropriate. An audible alarm and in particular a siren 22 responds to the CPU 17 comparing an input vital sign signal and finding that it is out of limits for patients requiring continuous or semi-continuous monitoring. The less severe situations do not trigger the siren 22.

Further as indicated in FIG. 1, the output of the CPU 17 can be sent to other stations 24 either in the same hospital or over a modem 25 to other locations. At these other stations, a remote server is located with its screen display 18 and, if desired, a siren. It is more efficient for there to be a single data storage 20 which stores all the information in the system. Data can also be received from other locations such as homes and nursing homes.

The Dynamic Data Exchange (DDE) driver is a program incorporated in the CPU 17 that allows communication with other devices and in particular provides a data distribution function in addition to support for the peripheral devices. The DDE driver program sends local digitized patient data to the monitoring program in the CPU 17 of the central server and to local work stations 24 and remote work stations. The DDE driver also provides ability to send commands from the CPU 17 to the various monitors 12. The DDE only communicates changes in data, thereby avoiding redundant transmissions.

Each medical monitor 12 comes with a standard output plug known as a RS232 plug to provide data appropriate to the central server 16. A standard converter 14 is employed which is known as a RS232 to RS485 interface converter. It is a commercially available item. It is plugged into the output of each medical monitor 12. The output of this converter 14 is transmitted in digital form over a two wire data grade telephone cable to an RS485 adapter at the input of the central server 16. In a preferred embodiment, a card is employed which has sixteen RS485 adapters on it as an input/output interface 15 to the CPU 12. Each RS485 on the card can connect to 32 telephone line pairs and thus to 32 medical monitors 12. Accordingly, the interface card 15 employed permits the central server 16 to receive continuous communication from up to 1,024 medical monitors 12.

It is contemplated that in a preferred embodiment, it might be possible to redesign a standard medical monitor 12 so that its output is compatible with the RS485 plug input to the central server 16 and in such a case the commercially available RS232 to RS485 converter 14 would not be needed.

Any one of a number of general purpose, multi-parameter portable or even non-portable monitor devices can be employed at each station to provide the multiple signals indicating the multiple vital signs being measured. One such device is sold by Datascope Corporation of 580 Winters Avenue in Paramus, N.J. under its trademark Passport.

Such multi-parameter monitoring devices can be selected to provide entirely non-invasive monitoring or a combination of non-invasive and invasive monitoring. The six vital signs are systolic, diastolic, pulse, respiration, temperature, and oxygen saturation. The sensors for these signs also make wave-forms and EKG readings available to user and/or server.

The interface converter 14 is manufactured by Black Box Corporation and another model is also made by South Hills Datacom. The RS485 interface which constitutes the individual components of the adapter 15 is manufactured by Quatech or by Emulex.

The CPU 17 incorporates a DDE driver which is a known type of device; one of which is the Texas Instruments Direct Driver RS-232. Another example of the DDE driver is the Siemens 3964R and the GE-FANU CC M2 Serial Port.

The CPU 17 itself can be an 80486 series PC-Compatible CPU with super VGA graphics card, super VGA touch-screen monitor, mouse, keyboard, sixteen megabytes of RAM and a minimum of two-hundred megabytes of hard drive together with a two gigabyte read-write laser disk drive. This laser disk drive need only be employed with the CPU 17 at the central server 16 and need not be employed with a local workstation PC 24 or remote workstation PCs.

The modem 25 can be a standard 14,400 bps V-32 bis modem.

The application program for this invention can be created by use of a process graphics software such as the InTouch software available from Wonderware Software Development Corporation of 16 Technology Drive in Irvine, Calif. With the InTouch software resident in the CPU 17, the user can generate the particular screen display arrangement shown in FIGS. 2 through 7 or any variation thereon. The techniques of generating the program for the particular screen displays illustrated herein are techniques that are known to those skilled in the art who employ a process graphics software package such as InTouch. The process graphics software remains resident in the CPU 17 as part of the applications operating system so that data from the monitors 12 can be applied to affect the screen displays 18 discussed in connection with FIGS. 2 through 7. An adequate set of programing instructions are set forth under an Appendix at the end of this specification.

Critical to the utility of this system in providing an enhanced degree of patient supervision are the displays made available on a display screen 18 at the central server 16 as well as on display screens that are in any remote work stations.

Figure 2:
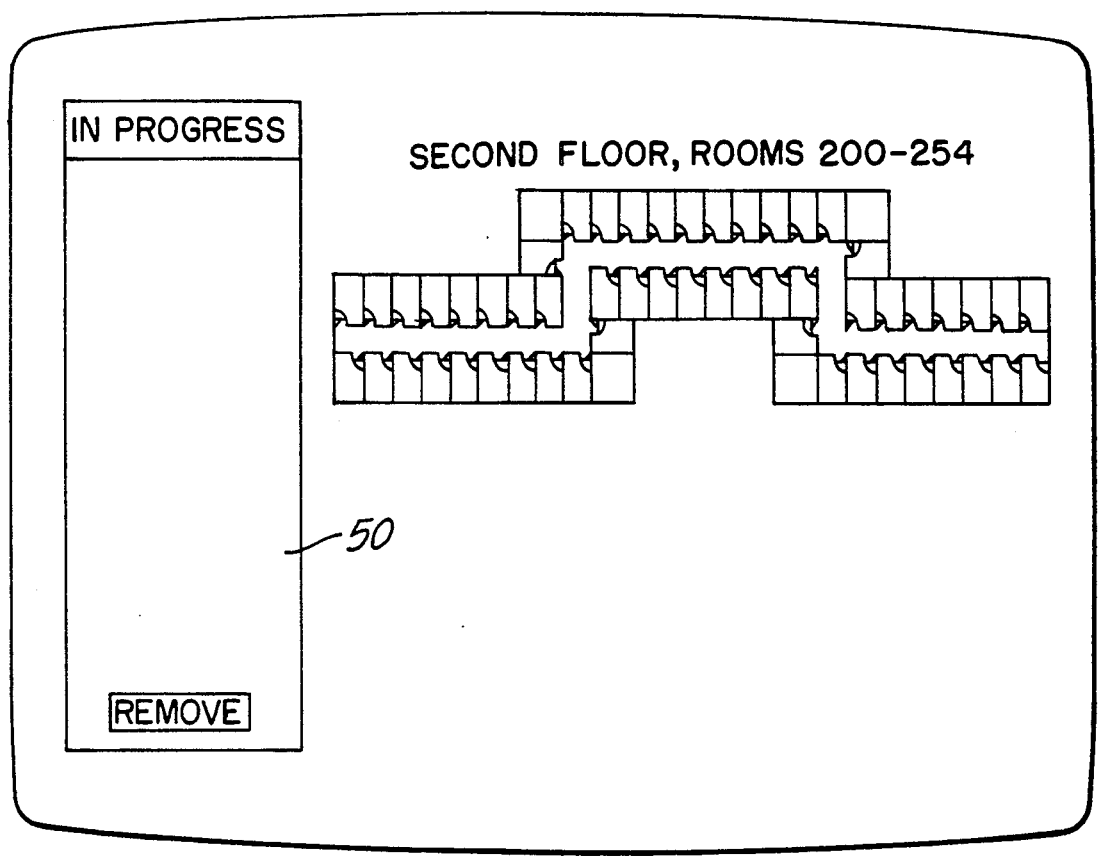
FIG. 2 illustrates a typical screen display which provides an overview of a floor in a hospital under normal conditions.

FIGS. 2 through 7 illustrate the displays made available. FIG. 2 shows a typical overview screen display in which a floor arrangement is shown with each room or site indicated by icons which are mapped to simulate the geometry of the floor. FIG. shows the overview screen when there is an alarm condition. Two windows are provided. The In Progress window 50 (having the titile bar 58) lists all alarms from the Notification States 1, 2 and 3 discussed below in connection with FIG. 6. The Notification States are a function of patient status and alarm severity. The window 50 lists alarms as a function of importance (the higher Notification States first) and within a Notification State in time sequence of occurrence. The window 50 provides an indication of the site or room involved and whether or not the out of limits situation is critical or if less serious indicates "warning". The In Progress window 50 also lists the nature of the vital sign which is out of limits and the time of occurrence.

Figure 3:
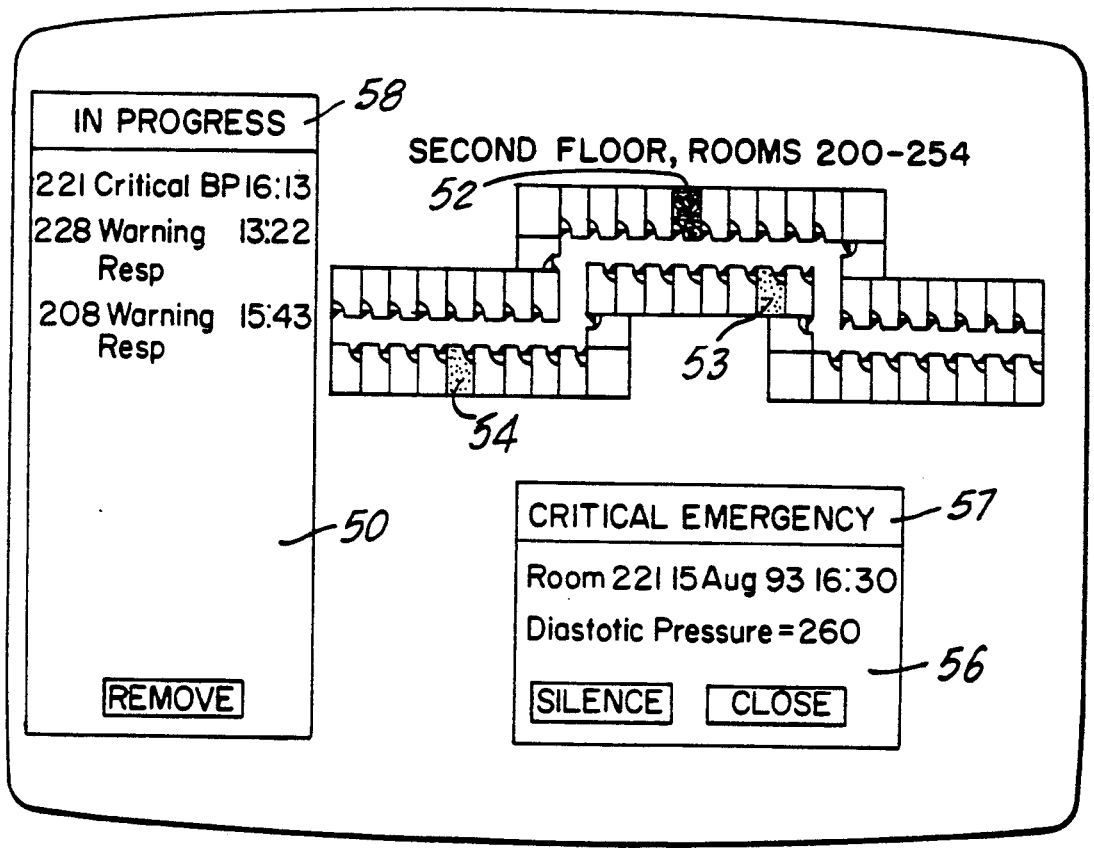
FIG. 3 is an illustration similar to that of FIG. 3 illustrating one critical alarm situation and two warning alarming situations.

As shown in FIG. 3, showing, Room 221, shown at reference number 52, has a critical blood pressure out of limits situation which occurred at 16:30 hours. Similarly, Room228, shown as reference number 53, has a warning out of limits situation (less serious than critical) with respect to the patient's respiration and that occurred at 13:22 hours. Room 208, shown at reference number 54, has a warning out of limits respiration problem that occurred at 15:43 hours.

On the same FIG. 3 screen, the Critical Emergency window 6 provides somewhat more detailed information concerning the critical situation in Room 221 and in particular shows that the blood pressure problem is that diastolic pressure is at 260. Because the critical emergency situations are accompanied by an audible siren, the FIG. 3 pop-up window 56 provides a touch zone designated "Silence" which permits the user to turn off the siren. The pop-up window 56 is an alarm window and will have the title "Critical Emerging" or "Off-Line Emergency" or "Warning Condition" as a function of the nature of the alarm.

Each window 50, 56 has a touch zone, "Remove" or "Close" to either remove all of the data in the In Progress window 50 or to close out the Critical Emergency window 56. The Remove button will only remove one of the alarms listed, and only if the alarm is not a critical alarm. User selects the alarm to be removed (using mouse-click, etc.) and then presses Remove button. Otherwise, alarms remain on the list until the conditions which triggered them cease. Alarms can be forced off the list by going to the individual room screen and altering the vital sign limits, signs monitored, or patient status.

It is important to note that certain colors are used to reinforce the information involved. Most of the sites are in a normal condition. They are in a green color (colors not shown in the Figures). The warning sites (Rooms 228 and 208) are shown in a yellow color and the critical site, Room 221, is shown in a red color. In addition, the title bar 57 of the Critical Emergency window 56 has a red background. The title bar 58 of the In Progress window 50 has a red background when there is a critical item in that window, a yellow background when there are only warning items in that window and a green background when the window is empty. In addition, the red room icon 52 will be a flashing red in order to attract attention. However, the yellow room icons 53, 54 will not be flashing. In addition, the color purple is used to indicate a disconnect of the vital sign sensor. This purple color off-line warning is in response to a null signal from the medical monitor. A null signal from the monitor will cause the central server 16 to generate a disconnect signal which can provide a unique audio alarm 22 and a unique (purple) color designation for the title bars 57 in the pop-up window 56 and on the relevant room icon. The background of the title bar 61 on the FIG. 5 zoom-in display will also be purple.

If there is more than one alarm condition requiring a pop-up window 56, multiple windows 56 will be shown, overlaid and offset to provide the observer with an indication that there is a plurality of windows 56 and to permit access to each window by whatever accessing technique is employed such as the mouse click.

Figure 4:
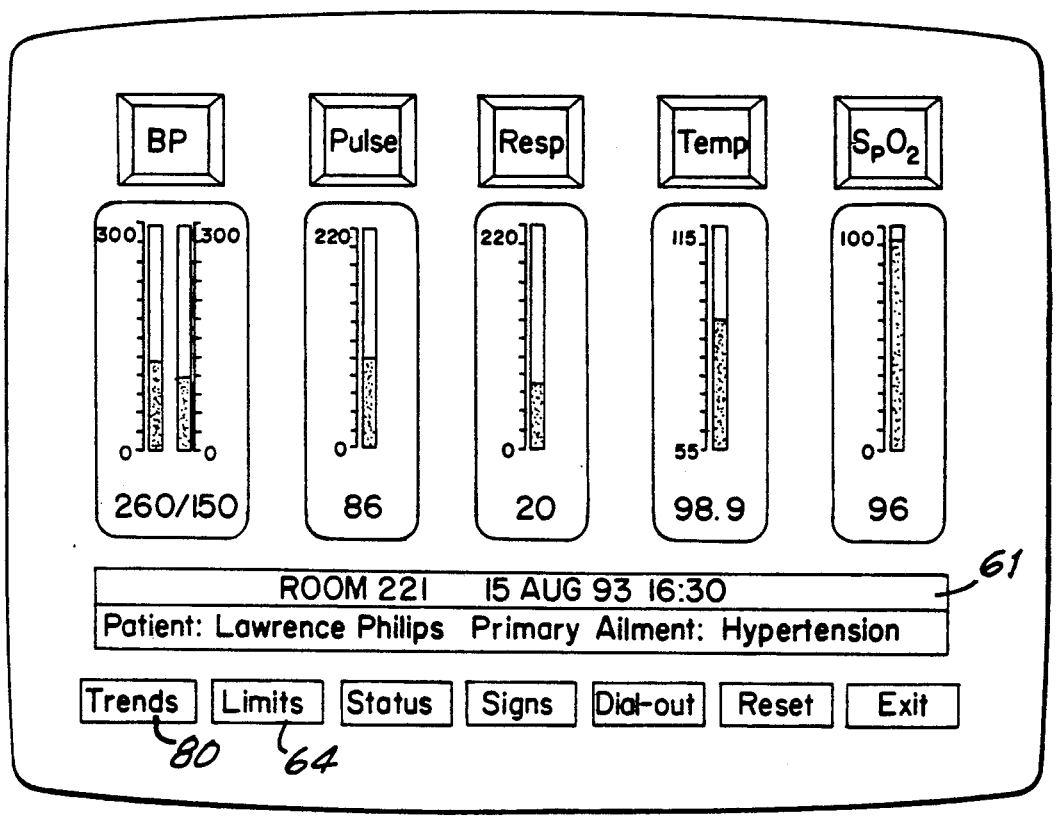
FIG. 4 illustrates a typical screen display of a particular patient site on the floor represented by FIG. 3 under normal conditions.
Figure 5:
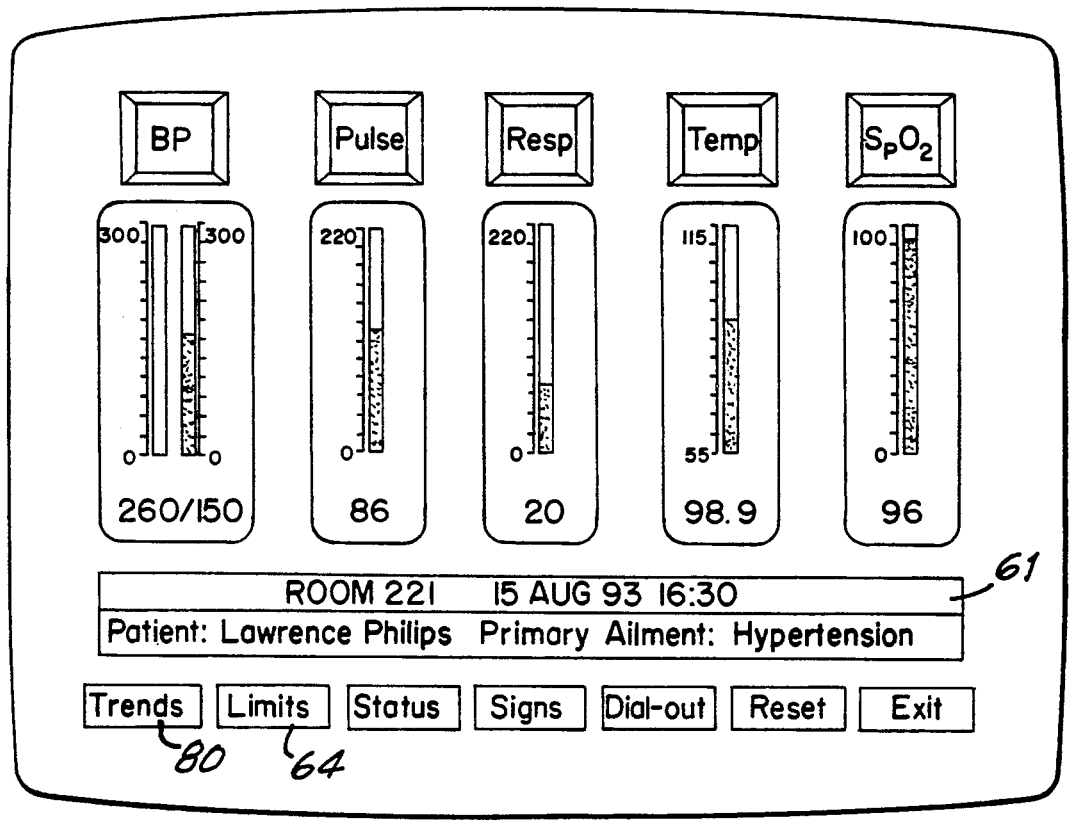
FIG. 5 is similar to FIG. 5 except that it shows a critical alarm situation at the patient site.

FIG. 4 indicates the screen display that could be called up for a particular room. This zoom-in screen display can be called up through a keyboard input of the room number or by an appropriate touch on the overview screen. FIG. 4 shows the non-alarm display for Room 221, corresponding to the FIG. 2 normal display condition. FIG. 5 shows the zoom-in display for the critical condition in Room 221, which critical condition is flagged by the FIG. 3 display. In FIG. 5, the BP (blood pressure) symbol 60 at the upper left is red and flashing indicating a critical condition. Each of the six vital signs is indicated in both analog and digital form. The patient is identified and the primary ailment is indicated.

In the normal FIG. 4 condition, the title bar 61 has a green background color and the icons indicating the various vital signs are green providing the vital signs are within the normal range. This use of green for normal condition helps to make sure that the yellow and red for lesser and greater level of emergency conditions stand out when they do occur. In FIG. 5, not only is the BP icon 60 red and flashing but the left column 62 representing diastolic pressure in analog form is also red and flashing. The rest of the vital sign icons and analog bar graphs are a normal green color representing a non-emergency condition.

This display arrangement shown in FIGS. 2 through 5 provides a useful trade-off of selection and focus in real time against a more comprehensive data presented in a less focused fashion and/or not being in real time.

Thus the overview screen of FIGS. 2 and 3 provides a real time indication that there is an emergency, where it is occurring, how severe the emergency is (that is, whether it is at a warning level or a critical level) and which type of vital sign function is out of line. The overview screen also provides a geographic presentation of where the emergency is.

The zoom-in screen (single site screen) of FIGS. 4 and 5 also provides all information in real time. However, it displays all of the functions and not only the function that is out of normal range. Furthermore, the zoom-in screen displays data in both digital form and analog form.

Furthermore, all program screens display information in both digital and analog form, showing both a numeric and abstract representation. This provides an intuitive grasp of the information presented, eliminating the time lag, confusion, and user error associated with information which must be skillfully interpreted.

By limiting the vital signs monitored to six, it becomes possible and feasible to monitor a large number of sites. Thus the system is particularly adapted to the general hospital situation more than to the intensive care unit situation (ICU). In an ICU situation, very specific and individual monitoring of many other parameters and conditions may be involved. But the cost and complexity of doing such makes the ICU type of situation inappropriate and in fact not used in the general hospital situation. More particularly, it is also the depth of information gathered from each sign that increases the data required dramatically, not just the number of signs monitored. The transmission and analysis of wave forms is what requires hundreds of times more processing power. However, it is useful only for a select few patients who are deemed critical enough to be placed in the high-cost ICU monitoring area. The six vital signs themselves are meaningful enough for most patients, and the number of patients who require this level of monitoring is a significant percentage of those occupying hospital rooms, a number many times greater than even the largest ICU's can handle.

The operational features which are critical to why this system is an improvement over anything presently known and in particular why it provides a meaningful monitoring of a large number of patients include the following:

1. The selection of a limited number of vital signs (six in particular).
2. The provision of a two stage alarm system based on a vital sign having passed a threshold wherein two separate thresholds are used to distinguish between a warning alarm and a critical alarm.
3. The display of a set of vital sign warning indicators in conjunction with the geographic display indicating where each patient is on a floor.
4. The ability to zoom-in on a patient site to obtain a display of more detailed information on the patient for whom there is either a warning condition or a critical condition.
5. The ability to grade the alarm importance as a partial function of patient's status.

In addition, because of the structure of the system, in which an intelligent central server is used in conjunction with a large number of dumb monitors, each one of which is in direct communication with the central server, the whole system becomes not only a good deal less expensive than other types of monitoring systems, but a good deal more fault tolerant and more flexible. Specifically, a broken lead or missing sensor will not adversely affect the operation of the rest of the system and a monitor can be moved around from site to site or patient to patient without requiring a reconfiguring of the system.

The combination of the above features, makes it economically feasible to provide significantly greater monitoring for individuals who are not appropriate for an intensive care unit and to provide such for as large a number of patients as is desired. It is feasible to achieve this extensive result because a reasonable amount of computer capacity and equipment is required. Thus extending significant and meaningful monitoring beyond those who are in an intensive care unit becomes economically feasible.

In addition the iconography of the display provides a particularly useful presentation of information to those who must monitor the situation leading to a more immediate recognition of where a warning situation exists, what the nature of it is likely to be and what individuals are involved.

Figure 7:
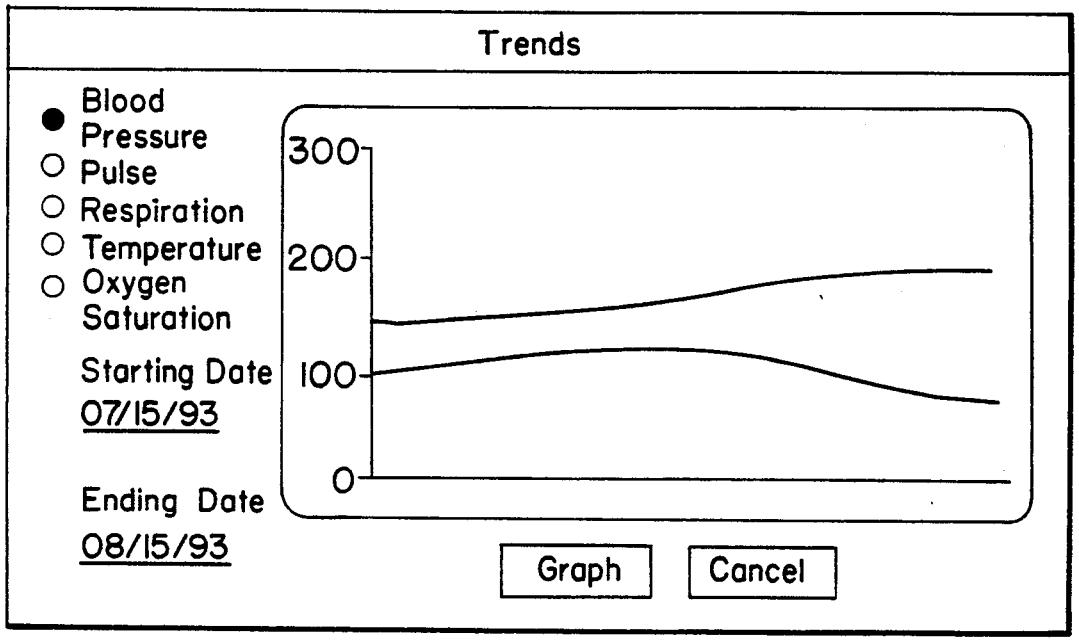
FIG. 7 illustrates a trends window which can be called up by the user to illustrate long term patient parameter trends.

The various pop-up windows of FIGS. 7 and 8 are provided to permit user modification of various parameters and selection of various options for a particular patient at a particular site.

FIGS. 4 and 5 show a series of seven "buttons" along the bottom of the screen. These buttons, which can be either click-on mouse cursor buttons or touch screen buttons, are actuated to call up the desired one of the windows shown in FIG. 6 or FIG. 7. The LIMITS button 64 will cause the "Set Vital Sign Limits" window 65 to appear. There is a normal default set of vital sign limits for adults. Actuating the adult button 66 and reset button 67 will cause that default set to appear. There is also a normal default child set of signs and a normal default senior set of signs and actuating the appropriate buttons 68 or 69 will cause those to appear. However, the individual user can tailor one or more of the vital sign limits by the usual use of a curser to locate the position on the screen where that limit is to appear and then keying in the desired limit. When the user has established the vital sign limits desired, actuating the "OK" button 70 will cause the screen to revert to the FIG. 4 zoom in state for that patient.

The "Set Vital Sign Limits" window 65 is important to enable the user to tailor the warning range and critical range of any one or more vital signs to what would be appropriate for a particular patient.

The other FIG. 6 windows are self-explanatory except the Patient Status window 70. The Patient Status window permits selecting the level of monitoring that is geared to the patient's condition. This is most important as it provides an important function in determining the Notification State discussed below.

The trends window of FIG. 7 is a pop-up window that can be accessed by actuating the trends button 80 in the lower left half corner of the screen as shown in FIG. 5. The particular vital sign that will be shown as a time line on the trends window for the particular patient can be selected by clicking on to the desired vital signs shown on the left portion of this window. In one embodiment, the default trend line is the one for the last twenty-four hours. However, the user can extend that time period by entering an appropriate starting date and ending date.

The selection of patient status in window 70 will partially determine how a particular out-of-limits or off-line condition is to be treated. A number of Notification States from most to least serious is provided. These Notification States can be grouped from most serious to a no—problem state as follows:

| NOTIFI-CATION STATE | PATIENT STATUS | VITAL SIGN CONDITION | ALARM SIGNALS PROVIDED |
|---|---|---|---|
| 1 | 2 Or 3 | Exceeds Critical Limits | Flashing Red & Siren |
| 2 | 3 | Off-Line | Flashing Purple & Siren |
| 3 | 2 or 3 | Exceeds Warning Limits | Solid Yellow & Siren |
| 4 | 1 | Exeeds Critical Limits | Solid Red |
| 5 | 1 | Exceeds Warning Limits | Solid Yellow |
| 6 | 2 | Off-Line | Flashing Purple |
| 7 | 1, 2, 3 | All Within Normal Limits | Solid Green |
| 8 | 1 | Off-Line | Solid Purple |
| 9 | 1, 2 or 3 | Sign Not Being Monitored | Solid Purple |

Notification States 1 through 8 ar only for those vital signs being monitored. If a vital sign is not selected on the window 72, then that sign will appear solid purple (Notification State 9) and the other Notification States will be provided in response to only those signs being monitored.

Appendix

The programming made possible by using commercially available program packages means that the following instructions would be adequate to permit one skilled in this art to create the system of this invention as described herein.

Instructions To Programmers

I. Guidelines:
   A. Create program screens with associated animation, icons, buttons, windows, and logic as described in the section Characteristics and Logic for Program Screens, and pictured in the sections Full-screen Views, and Pop-up Window Views.
   B. Connect all objects to the data they describe.
   C. Set default values for room parameters. note: both default values, and all room parameter values, will be kept in only one place, e.g. on the central server. Values can be changed from any workstation on the network.
   D. Add data storage logic for data and alarms:
      1. Signs database shall contain patient name, room number (221a for first bed in room 221, 221b for second bed, etc), date, time, and all sign values.
      2. Signs will be stored to disk every fifteen minutes.
      3. Alarms (Notification States 1-3) database shall contain room number, nature of alarm (warning, critical, off-line), date, time, and all sign values.
      4. Alarms will be stored in the alarms database as they occur.
   E. Add Security-Logic:
      Levels of security clearance are as follows:
      1. View all screens, silence alarms.
      2. Above, plus use of buttons on Individual Bed Screen, close alarms, and remove alarms ( from-in-progress list).
      3. Above, plus set overall parameter defaults.
II. Characteristics and Logic for Program Screens
   A. Overview Screen:
      1. Bed I cons Displays one icon for each bed monitored, icons being positioned on screen according to floor plan, including hallways, etc., to create a facility map (can be for entire building, or just one floor).

If a room has only one bed, the bed icon will show up on the map as being the size and shape of the room which contains it.

In the event that more than one bed is located in a room, the bed icons will be placed together to form the shape of the room which contains them.

Selecting a bed icon brings up its individual Bed screen (see next section).

Color/animation conventions:
   Bed icons shall obey color/animation conventions listed in individual Bed screen section.
   Animation and color of bed icon shall match the Notification State of the most critical vital sign icon for that particular bed.
   Lower numbers represent more critical Notification States.

2. Alarms:
   Notification States 1, 2 and 3 will be considered alarms. Alarms shall sound audio signal, display pop-up alarm window, and appear in the Alarms-in progress window.
   Alarms will also activate the following dial-out options, if the options are selected: 1) Deliver alarms to central station, 2) Deliver alarms to pager.
   Audio signals for critical, warning, and off-line will have different volume levels and different sound patterns.

3. Pop-up alarm window shall include:
   Title bar displaying the nature of alarm i.e., Critical, warning, or off-line.
   Color of title bar shall match the conventions for the Notification State of the alarm it describes.
   Room number.
   Date and time.
   Description of problem (e.g., Diastolic pressure=260).
   Silence alarm button turns off audio alarm signal
   Close alarm button turns off audio alarm signal, and closes pop-up alarm window, but room remains in animation until alarm conditions cease (can be forced by changing limits in patient's individual bed screen).

4. Alarms-in-progress window (left side of screen)
   Color of title bar shall match the conventions for the Notification State of the most critical alarm listed.
   Lists alarms in progress, by category ( critical, then off-line, then warning), and within each category, by time of occurrence ( oldest to newest).
   Each list entry will show room number, nature (critical, etc.), sign, and time of occurrence.
   Window also has remove button which allows user to delete entries from list.
   Individual entries can be deleted only if they are warning or off-line alarms; entries describing critical alarms will remain until alarm conditions cease (can be forced by changing limits).

B. Individual Bed Screens
   1. Vital Sign Icons:

One icon for each sign monitored, positioned in a horizontal row at the top of the screen.

Icons shall obey the following color conventions.

2. Color conventions:

Notification State 9: Steady purple if sign is selected not to be monitored.

Notification State 8: Steady purple if sign is off-line (patient status level 1).

Notification State 7: Steady green if sign is within normal limits.

Notification State 6: Flashing purple if sign is off-line (patient status level 2).

Notification State 5: Steady yellow if sign exceeds warning limits (patient status level 1).

Notification State 4: Steady red if sign exceeds critical limits (patient status level 1).

Notification State 3: Steady yellow if sign exceeds warning limits (patient status levels 2, 3).

Notification State 2: Flashing purple if sign is off-line (patient status level 3).

Notification State 1: Flashing red if sign exceeds critical limits (patient status levels 2, 3).

3. Faceplates:

One faceplate for each sign monitored, positioned under the associated icon.

Display the numerical value of monitored sign at bottom of faceplate.

Display a vertical bar graph representation of monitored sign above numerical value.

Bar graph shall include an axis labeled with appropriate units.

Bar graph shall follow color conventions.

4. ID Window:

Title bar shall include room number, date, and time.

Title bar background shall follow color conventions (background shall change animation state to match the most critical icon animation state, see color conventions above).

Window shall display patient name and primary ailment (interface with external database).

Buttons:

Buttons in horizontal row at bottom of screen.

Exit button closes window and returns to overview screen.

Trends button:

Allows user to view historical trends of monitored vital signs.

Displays pop-up window displaying starting date, and finish date for trend graph.

Also shows list of vital signs with radio buttons to choose which sign will be graphed.

Includes Cancel and Graph buttons.

6. Limits button:

Allows user to set both upper and lower warning and critical limits for any or all signs.

Displays pop-up window listing each sign, its upper and lower warning limits, and its upper and lower critical limits.

Pop-up window includes buttons for OK, cancel, reset (to default limits), and radio button for child/adult/senior.

7. Signs button:

Allows user to choose which signs are monitored (e.g. patient may only need to have BP and pulse monitored).

Displays a pop-up window showing the list of vital signs, with OK and cancel buttons.

Includes a check box for each sign, and one for all signs (checking this turns all signs on).

8. Status button:

Allows user to determine how Notification States are handled.

Displays pop-up window with OK and cancel buttons.

Radio buttons let user select one of three status levels level 1: patient receiving sporadic monitoring (patient has signs checked by hooking up to a monitor from time to time, e.g. an outpatient).

level 2: patient receiving semi-continuous monitoring (patient may disconnect from time to time, may be ambulatory, e.g. someone in for overnight observation).

level 3: patient receiving continuous monitoring (patient must always be connected to monitor, is not ambulatory).

9. Dial-out button:

Determines how application will notify parties of signs and alarms for particular bed.

Displays pop-up window including OK and cancel buttons.

Also shows checklist for the following three dial-out options, with a separate phone number displayed next to each option.

Deliver signs to central station—if checked, application will dial associated number periodically to deliver sign values to another Solowatch system.

Deliver alarms to central station—if checked, application will dial associated number and deliver all alarms to another Solowatch workstation. For Notification States 1, 2 and 3 only.

Deliver alarms to pager—if checked, application will dial associated number and deliver alpha-numeric alarm message to pager (same message as shown in Alarms-in-progress window). For Notification States 1, 2 and 3 only.

Phone numbers can be edited at any time.

10. Reset button:

Resets all bed parameters to default values.

Displays pop-up window cautioning user that all signs will be reset to defaults.

Affects patient status, signs selected, warning and critical limits, patient age, and communications options.

Also displays buttons for OK and Cancel.

For security purposes, defaults (which are determined by the user) can be changed only by altering application.

Typical defaults might be as follows:
    Patient status=level 1.
    Signs selected=all.
    Patient age=adult.
    Communications=no dial-outs.
    Warning and critical limits=as determined by user.

What I claimed is:

1. A medical monitoring system comprising:

a plurality of individual site vital sign monitors, each of said monitors providing a plurality of vital sign signals for each of said plurality of sites, a central processing unit, said vital sign signals from each of said site monitors being coupled as inputs to said central processing unit;

a display screen coupled to outputs from said central processing unit;

an overview display on said screen, said display including a topological presentation of each of said sites and a first set of icons, each icon of said first set representing a separate one of said sites, a plurality of vital sign states for each of said vital signs at each of said individual sites, each of said vital sign states providing an indication of the relative significance of the vital signal being measured by a monitor relative to a predetermined vital sign value limit, means to set a patient status state at each of said sites, a set of Notification States to rank the relative importance of the vital state occurring at each of said individual sites as a partial function of said patient status state and a partial function of said vital sign state, and a set of alarm signals indicating said Notification States, said alarm signal employing said first set of said icons to provide site identification of the Notification State involved.

2. The medical monitoring system of claim 1 wherein said plurality of vital sign states includes:

a critical state indicating that a vital sign value is outside of a second set of predetermined value limits, said second set of value limits being narrower than said first set of value limits, and an off line state indicating that a vital sign monitor is not providing a signal.

3. The medical monitoring system of claim 1 wherein said set of Notification States includes:

first subsets of said Notification States indicated by alarm signals which include (i) site specific ones of said first set of icons to identify the site involved, (ii) an auditory alarm and (iii) a site-specific pop-up window on said overview display, said pop-up window including identification of the vital sign which is the basis of the Notification State involved, second subsets of said Notification States indicated by alarm signals which include site specific ones of said first set of icons flashing on said screen to identify the site involved, third subsets of said Notification States indicated by alarm signals which include site specific ones of said first set of icons providing a color change on said screen to identify the site involved.

4. The medical monitoring system of claim 2 wherein said set of Notification States includes:

first subsets of said Notification States indicated by alarm signals which include an auditory alarm and a site-specific pop-up window on said screen, said pop-up window including identification of the vital sign which is the basis of the Notification State involved, second subsets of said Notification States indicated by alarm signals which include site specific ones of said first set of icons flashing on said screen, third subsets of said Notification States indicated by alarm signals which include site specific ones of said first set of icons providing a color change on said screen.

5. The medical monitoring system of claim 2 further comprising:

a second set of icons providing an indication of said vital sign status, said second set of icons including an indication of the ones of said vital sign states that are represented by the Notification State involved, a third set of icons providing an indication of patient vital sign values, and an operator actuated zoom-in presentation on said display screen for a particular site on said overview display, said zoom-in presentation including icons from said second and third sets of icons.

6. The medical monitoring system of claim 4 further comprising:

a second set of icons providing an indication that a vital sign is outside of said predetermined value limits, said second set of icons including an indication of the one of said vital sign states of whatever vital sign is outside of said predetermined value limits, a third set of said icons providing indication of patient vital sign values, and an operator actuated zoom-in presentation on said display screen for a particular site on said overview display, said zoom-in presentation including icons from said second and third sets of icons.

7. The medical monitoring system of claim 2 further comprising:

a normal vital sign state to indicate a vital sign within limits condition wherein the vital sign value is within said second set of predetermined value limits.

8. The medical monitoring system of claim 4 further comprising:

a normal vital sign state to indicate a vital sign within limits condition wherein the vital sign value is within said second set of predetermined value limits.

9. The medical monitoring system of claim 5 further comprising:

a normal vital sign state to indicate a vital sign within limits condition wherein the vital sign value is within said second set of predetermined value limits.

10. The medical monitoring system of claim 6 further comprising:

a normal vital sign state to indicate a vital sign within limits condition wherein the vital sign value is within said second set of predetermined value limits.

11. The medical monitoring system of claim 3 further comprising:

an alarms-in-progress window on said screen listing predetermined ones of said Notification States at each of said sites.

12. The medical monitoring system of claim 4 further comprising:

an alarms-in-progress window on said screen listing predetermined ones of said Notification States at each of said sites.

13. The medical monitoring system of claim 6 further comprising:

an alarms-in-progress window on said screen listing predetermined ones of said Notification States at each of said sites.

14. The medical monitoring system of claim 8 further comprising:
an alarms-in-progress window on said screen listing predetermined ones of said Notification States at each of said sites.

15. The medical monitoring system of claim 10 further comprising:
an alarms-in-progress window on said screen listing predetermined ones of said Notification States at each of said sites.

16. The method of medically monitoring a plurality of patients at a plurality of sites comprising the steps of:
on a display screen, providing a topological presentation of each of said sites,
employing a first set of icons, each of said icons representing a separate one of said sites, on said topological presentation,
at each of said sites, substantially continuously measuring a plurality of predetermined vital sign values to provide a set of vital sign signals for each of said sites,
simultaneously comparing each of said vital sign values to predetermined value limits to provide a plurality of vital signal states at each of said sites indicating relative significance of any out of normal vital sign values,
providing a patient status state at each of said sites,
providing a set of Notification States to rank the relative importance of the vital sign state occurring at each of said individual sites as a partial function of said patient status state and a partial function of said vital sign state,
providing a set of alarm signals to indicate said Notification States,
employing said first set of icons as part of said set of alarm signals to provide site identification of the Notification State involved.

17. The method of claim 16 wherein said step of providing a set of Notification States includes the steps of:

providing a first subset of said alarm signals to indicate a first subset of said Notification States including changing a characteristic of site specific ones of said first set of icons to identify the site involved, providing an auditory alarm and providing a site specific pop-up window on said overview display, said pop-up window including identification of the vital sign which is the basis of the Notification State involved,
providing a second subset alarm signals to indicate a second subset of said Notification States including a flashing presentation of site specific ones of said first set of icons to identify the site involved,
providing a third subset of said alarm signal to indicate a third subset of said Notification States including changing the color of site specific ones of said first set of icons to identify the site involved.

18. The method of claim 17 comprising the further steps of:
within said plurality of vital sign states, providing (i) a critical state indicating that a vital sign is outside of a first set of predetermined value limits, (ii) a warning state indicating that a vital sign is outside of a second set of predetermined value limits, said second set of value limits being narrower than said first set of value limits, and (iii) providing an off-line state indicating that a vital sign monitor is not providing a signal,
providing a second set of icons to indicate the ones of said vital sign states that are represented by one of said Notification States,
providing a third set of icons to indicate the patient vital sign values represented by the Notification State involved, and
providing a zoom-in presentation on a display screen for a particular site on said overview display and employing said first and second set of icons in said zoom-in presentation.

* * * * *